(12) United States Patent
Davey (10) Patent No.: US 8,075,531 B2
(45) Date of Patent: Dec. 13, 2011

(54) MODULAR IMPLANTABLE MEDICAL DEVICE

(75) Inventor: Christopher Davey, Dublin (IE)

(73) Assignee: Marvao Medical Ltd., Galway (IE)

( * ) Notice: Subject to any disclaimer, the term of this patent is extended or adjusted under 35 U.S.C. 154(b) by 0 days.

(21) Appl. No.: 12/174,582

(22) Filed: Jul. 16, 2008

(65) Prior Publication Data

US 2010/0016835 A1  Jan. 21, 2010

(51) Int. Cl.
*A61M 5/32* (2006.01)
*A61M 31/00* (2006.01)
*A61M 25/16* (2006.01)

(52) U.S. Cl. ............... 604/175; 604/174; 604/93.01; 604/533; 604/535

(58) Field of Classification Search ............ 604/288.01, 604/93.01, 533–535, 175, 174, 892.1, 500, 604/539; 623/12, 11
See application file for complete search history.

(56) References Cited

U.S. PATENT DOCUMENTS

| | | | |
|---|---|---|---|
| 4,266,999 A | 5/1981 | Baier | |
| 4,405,305 A | 9/1983 | Stephen et al. | |
| 4,488,877 A | 12/1984 | Klein et al. | |
| 4,668,222 A | 5/1987 | Poirier | |
| 4,897,081 A | 1/1990 | Poirier et al. | |
| 4,935,004 A | 6/1990 | Cruz | |
| 5,098,397 A | 3/1992 | Svensson et al. | |
| 5,100,392 A | 3/1992 | Orth et al. | |
| 5,242,415 A | 9/1993 | Kantrowitz et al. | |
| 5,662,616 A | 9/1997 | Bousquet | |
| 5,685,878 A | 11/1997 | Falwell et al. | |
| 5,766,249 A * | 6/1998 | Griffith | 600/30 |
| 5,823,994 A | 10/1998 | Sharkey et al. | |
| 5,830,184 A | 11/1998 | Basta | |
| 5,848,987 A | 12/1998 | Baudino et al. | |
| 5,882,341 A | 3/1999 | Bousquet | |
| 5,989,213 A | 11/1999 | Maginot | |
| 6,033,382 A | 3/2000 | Basta | |
| 6,264,673 B1 | 7/2001 | Egnelov et al. | |
| 6,520,949 B2 * | 2/2003 | St. Germain | 604/500 |
| 6,719,724 B1 * | 4/2004 | Walker et al. | 604/113 |
| 2004/0236314 A1 * | 11/2004 | Saab | 604/539 |
| 2007/0225642 A1 * | 9/2007 | Houser et al. | 604/93.01 |

OTHER PUBLICATIONS

Raad, et al,. Arch Internal Medicine, "Intravascular Catheter-Related INfections: New Horizons and Recent Advances",vol. 162, pp. 871-878, Apr. 2002.

* cited by examiner

*Primary Examiner* — Kevin C Sirmons
*Assistant Examiner* — Bradley Thomas, Jr.
(74) *Attorney, Agent, or Firm* — Pierce Atwood, LLP; Kevin M. Farrell, Esq.; Katherine A. Wrobel, Esq.

(57) ABSTRACT

The present invention is a modular implantable medical device that is used deliver materials or energy into a patient's physiology, or from one region of a patient's physiology to another. The device includes a port element with a passageway therethrough for directing and anchoring a conduit element in a desired location. Both elements can be adjusted during placement to maximize the safety, comfort, and efficacy of use. In one embodiment, the port element is comprised of two components such that the passage way is formed after the components are assembled. This modularity enables a large diameter section of the conduit to be advanced past the port location, and the port to be assembled about a smaller proximal section of the conduit, thereby establishing full contact between the port and conduit elements to anchor the device in an optimal position.

25 Claims, 7 Drawing Sheets

MODULAR IMPLANTABLE MEDICAL DEVICE

BACKGROUND OF THE INVENTION

1. Field of the Invention

The present invention relates generally to the field of medical devices and in particular to the field of long term, implantable devices for permitting access to a patient's inner physiology.

2. Summary of the Related Art

Medically treating a patient often requires long term placement of a medical device across one or more organ systems to establish access to a specifically targeted interior body site for diagnostic or therapeutic purposes. One common example is the establishment of percutaneous vascular access for purposes of administering liquid therapeutic agents, removing bodily fluids for testing or monitoring, treating bodily fluids before being returned to the body, and/or disposing of bodily fluids.

Particularly in the case of administering fluids to, or removing fluids from, the body continuously or periodically over an extended time period, those skilled in the medical arts typically use what are known as "permanent" catheterization techniques. These techniques employ implanted devices such as tunneled central venous catheters (CVCs) that remain implanted for durations ranging from a few weeks to years. Examples of such implanted and related medical devices exist in the following references, which are incorporated herein by reference: U.S. Pat. No. 4,266,999 (Baier); U.S. Pat. No. 4,405,305 (Stephen et al.); U.S. Pat. No. 4,488,877 (Klein et al.); U.S. Pat. No. 4,668,222 (Poirier); U.S. Pat. No. 4,897,081 (Poirier et al.); U.S. Pat. No. 4,935,004 (Cruz); U.S. Pat. No. 5,098,397 (Svensson et al.); U.S. Pat. No. 5,100,392 (Orth et al.); U.S. Pat. No. 5,242,415 (Kantrowitz et al.); U.S. Pat. No. 5,662,616 (Bousquet); U.S. Pat. No. 5,823,994 (Sharkey et al.); U.S. Pat. No. 5,830,184 (Basta); U.S. Pat. No. 5,848,987 (Baudino et al.); U.S. Pat. No. 5,882,341 (Bousquet); U.S. Pat. No. 5,989,213 (Maginot); and U.S. Pat. No. 6,033,382 (Basta). Examples of therapeutic regimens requiring such long-term continuous or periodic access to a specific internal body location include parenteral feeding, chemotherapy, antibiotic administration, dialysis, and chronic anesthesiology.

Generally, the type of procedure that a patient requires dictates whether a physician will utilize an acute, short term catheterization technique, or a chronic, long term catheterization technique. For example, establishing a state of general anesthesiology in preparation for a surgical procedure typically involves placing a CVC in a patient's blood vessel for a relatively short period of time, such as a few minutes to a few hours, and then removing the catheter once the surgery is finished and the patient is revived. When performing such an anesthesiology procedure, a physician commonly uses a short term catheterization technique to place a drug delivery catheter in a blood vessel of the patient.

In direct contrast to this example of short term CVC placement, a physician performing a hemodialysis procedure in a patient suffering from chronic kidney failure may place a CVC in one of the patient's blood vessels for a relatively long period of time. Such a patient typically requires dialysis sessions three times per week for an indefinitely extended period of time. Healthy kidney function ensures removal of fluid, chemicals, and wastes typically filtered from a person's blood. Hemodialysis removes these elements by sending a patient's blood to an external artificial kidney machine via the permanent vascular access, often established by placement of a long term catheter within the patient. A patient who is involved in such a hemodialysis regimen may need a catheter placed in a blood vessel for weeks, months, or years in order to provide a ready means for vascular access into that patient's bloodstream to enable these frequent life saving dialysis treatments.

Long term catheterization techniques typically entail inserting a catheter into a patient using a "tunneled catheter technique." This procedure involves inserting a long term catheter into the patient through an incision in the skin and then routing the catheter for several centimeters under the skin before entering deeper regions of the body. Despite routine use, conventional tunneled catheter designs seriously compromise the ability of a patient's skin to protect the patient's body from infection. As discussed in "Intravascular Catheter-Related Infections: New Horizons and Recent Advances" (Raad et al., *Arch Internal Medicine/Vol* 162, Apr. 22 2002, Pages 871-878.), catheter-related infections are frequent events and present a potentially fatal health problem. High morbidity rate and high procedural cost are characteristics of typical long term tunneled catheter usage. The primary reason that the use of conventional catheters leads to a high rate of infection is that microorganisms enter the body through the skin incision. A conventional tunneled catheter device may include a tissue ingrowth cuff that acts as a barrier for micro-organisms entering the body and that anchors the catheter in the subcutaneous tunnel. Such a conventional device, however, still fails to prevent undesirably high infection rates. This is because standard cuff designs are designed for positioning within a subcutaneous tunnel rather than at the skin entry site, which is the most effective location at which to position a tissue ingrowth cuff for preventing infection.

Furthermore, in order to function properly over extended periods of time, many types of long term tunneled catheters require placement of their tips in a very specific high blood flow location, typically the Superior Vena Cava/Right Atrial Junction (SVC/RA). The turbulent flow in this location ensures rapid mixing and systemic distribution of therapeutic agents throughout a patient's vascular system, and also minimizes the risk of thrombus forming on the catheter's tip and leading to catheter dysfunction. Skilled clinicians are acutely aware of the need for highly precise catheter tip placement because they frequently diagnose and resolve catheter complications associated with improper tip placement. With conventional tunneled catheter designs, the ability to precisely adjust the position of the catheter tip in the SVC/RA depends largely on a freedom to position and adjust the tissue ingrowth cuff anywhere along the length of a subcutaneous tunnel.

Some tunneled catheter devices include adjustable dermal tissue ingrowth cuff assemblies. For example, the apparatus and methods disclosed in U.S. Patent Application No. 2004/0236314 to Mark A. Saab (Saab), incorporated herein by reference, allow a physician to place a modular dermal tissue ingrowth cuff assembly precisely within a skin incision site and subsequently adjust the location of the distal (internal) tip of a catheter assembly associated with the tissue ingrowth cuff assembly. This device comprises a base (or port) having tissue ingrowth material thereon for securely anchoring the port at the incision site. A physician using such a device, therefore, has the ability to position the catheter tip precisely at the desired body site without disturbing, moving, or stressing the fixed tissue ingrowth cuff. Positioning the modular tissue ingrowth cuff at the skin incision site enables the skin to heal into the device, and regain its ability to protect the patient from infection.

Such advanced tissue ingrowth cuff assemblies have resulted in numerous improvements related to patient care and well being, but they fail to anticipate or address several practical implementation issues. First, these existing devices typically require one or more conduit connections to the port (base) to establish a continuous and reliable sealed fluid path between the inner and outer regions of the patient's body. A clinician implanting such a device and connecting conduits to the base (port) disposed within a subcutaneous pocket is unable to see the connection points during assembly and after assembly to ensure proper, secure connections. This problem is increasingly serious with small devices because the clinician loses a significant tactile advantage during assembly. Second, incorporating multiple connection mechanisms into the base (port) complicates assembly and creates more junctions at which the device may fail. Third, having multiple mechanical connections to the base (port) prolongs the medical procedure and unnecessarily complicates the adjustment of the device to suit a patient's physiology. Also, these devices fail to enable a clinician to determine where to trim the conduit to ensure proper distal tip placement within a patient's anatomy. Requiring a clinician to connect one or more elements to the port therefore increases difficulty of use, increases manufacturing cost, prolongs the medical procedure, and, most importantly, decreases reliability of the device.

A need therefore exists for a subcutaneous port that anchors a transcutaneous conduit, protects a patient from infection, and requires no conduit fluid path connections to the port. Furthermore, in cases requiring modular conduit, for example when the distal tip requires precise placement, a need exists for a device that supports a modular conduit having a single fluid path connection point inside the patient's physiology. A further need exists for a device that enables making and testing that conduit-to-conduit connection for proper assembly outside the patient's body within a clinician's view prior to positioning the connected modular conduit inside the patient's physiology. Lastly, a need exists for a device that facilitates using a simple and precise method of predetermining where to trim the conduit along its length prior to making the conduit-to-conduit connection to ensure proper final distal tip placement.

SUMMARY OF THE INVENTION

The present invention comprises a medical device that is capable of implantation within a patient for long-term treatments, such as catheterization procedures, and a method of using the device. The device of the present invention includes a base that functions as an implanted medical port capable of receiving, routing, and anchoring a treatment component, such as for example a fluid conduit, power cable, or fiber optic cable, that extends through the patient's skin into the patient's internal physiology. The port is shaped to maximize comfort and ease of installation, and thus a relatively flat and generally rectangular geometry is most preferable for a variety of applications. The device of the present invention is adapted to support, direct, and anchor the treatment component such that no fluid or energy connections are required between the port and the treatment component to provide diagnostic or interventional treatments. Thus, fluid or energy in the form of light, heat, microwaves, and radio frequency (RF) transmissions, for example, can be transported to or from the patient in a controlled manner through the treatment component without coming into direct contact with the port. The port and the treatment component are further equipped with tissue ingrowth surfaces that help further anchor the device and establish a biological seal between living tissue and the regions of the treatment device on either side of the port.

One embodiment of the device of the present invention comprises a unitary port equipped with a passage therein for receiving a flexible treatment component entering through one outer surface of the base and exiting through another surface. The passage through the port is sized such that the section of flexible treatment component passing through the port is in full contact with at least one portion of the port, preferably the surface at which tissue ingrowth is desired. Additionally, the passage through the port may guide a flexible treatment component supported therein in a non-linear and/or angled direction that optimizes the device's performance and patient comfort.

Another embodiment of the present invention comprises a modular implantable port for stabilizing a treatment component for long-term use. The modular implantable port comprises a first and second element designed for reversible engagement around a continuous portion of a treatment component, such as a conduit or electrical lead. The first element comprises engagement elements which cooperate with counterpart engagement elements on the second element for aligning and securely but reversibly engaging the second element with the first element. The first and second elements each further comprise a portion of a wall defining a support passageway and which cooperate to define a support passageway when the first and second elements are assembled in an engaged state. The support passageway is formed by assembling the first and second elements and is sized to accommodate a continuous portion of a treatment component. In some embodiments, the device further comprises a tissue ingrowth cuff material fixedly disposed on a surface of one or both of the first and second elements for securing the modular implantable port to adjacent tissue, such as but not limited to subcutaneous dermal tissue.

In another embodiment, the treatment component is a flexible conduit comprised of a proximal portion that passes through a subcutaneously placed port and terminates outside of the patient's body, and a distal portion that terminates inside the patient's body at a specific, more distal location chosen by the clinician. The flexible conduit may be modular such that the proximal portion and the distal portion may be connectable by a fastening means. A clinician may trim and connect the modular portions of the conduit independent of interactions with the port as part of the placement procedure within the patient.

In all embodiments, the utility of the device optionally may be enhanced by incorporating markings on one or more portions of the treatment component to establish a graduated series of reference points for measuring and trimming. A clinician may use these markings in conjunction with patient's physiological landmarks to adjust, modify, and otherwise optimize the placement of the device within the patient to maximize comfort, safety, and efficacy.

These and other features and advantages of embodiments of the present invention are described in greater detail below with reference to the following figures.

DETAILED DESCRIPTION

The present invention provides a medical device that is capable of implantation within a patient for long-term treatments. The device of the present invention includes a base that functions as an implanted medical port capable of receiving, routing, and anchoring a treatment component, such as for example a fluid conduit, power cable or fiber optic cable, that extends through the patient's skin into the patient's internal physiology. The port is shaped to maximize comfort and ease of installation, and thus a relatively flat and generally rectangular geometry is most preferable for a variety of applications. The device of the present invention is adapted to support, direct, and anchor the treatment component such that no fluid or energy connections are required between the port and the treatment component to provide diagnostic or interventional treatments. Thus, fluid or energy in the form of light, heat, microwaves, and radio frequency (RF) transmissions, for example, can be transported to or from the patient in a controlled manner through the treatment component without coming into direct contact with the port. The port and the treatment component are further equipped with tissue ingrowth surfaces that help further anchor the device and establish a biological seal between living tissue and the regions of the treatment device on either side of the port.

Figure 1:
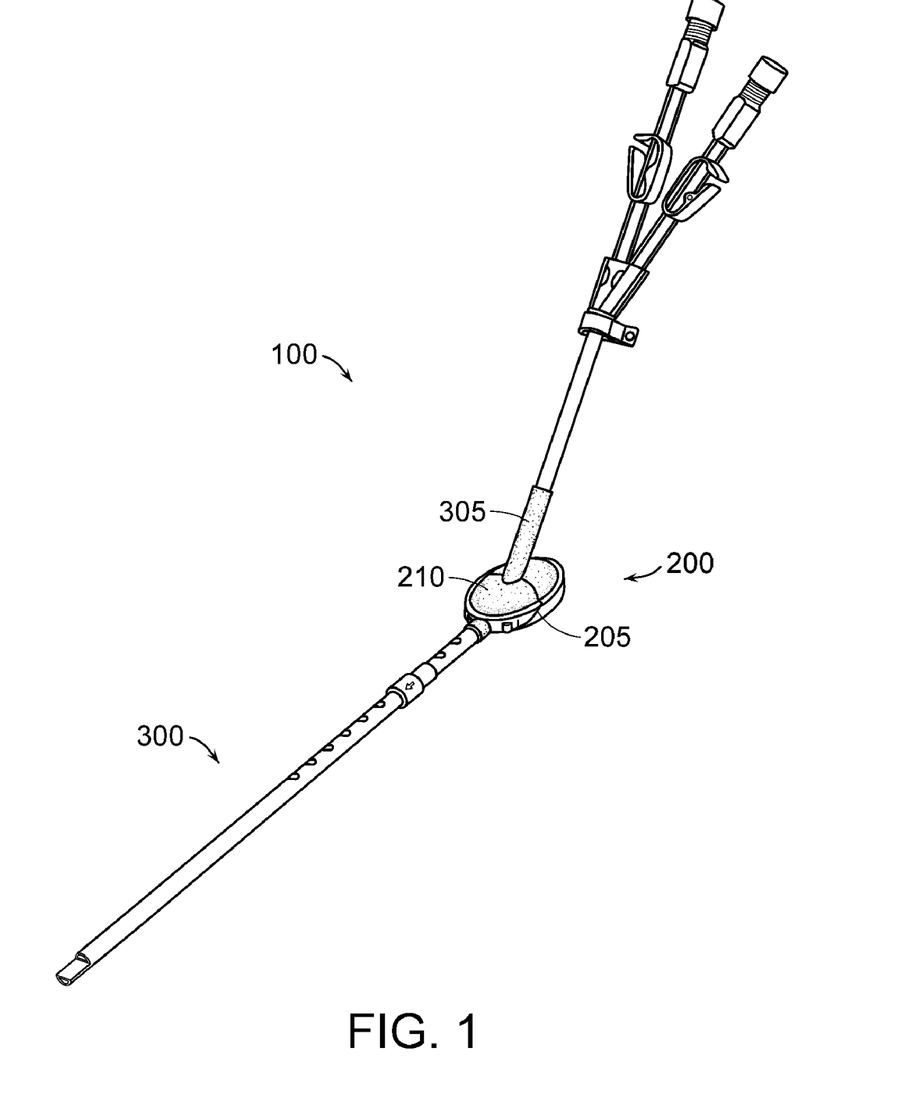
FIG. 1 depicts a general perspective view of an embodiment of the medical system the present invention.

As FIG. 1 depicts, one embodiment of the present invention comprises a system 100 that provides long-term access to the inner physiology of a patient. One such application of this system 100 is providing long-term vascular access for various kinds of catheterization and/or dialysis procedures. In particular, the system 100 comprises an implantable device 200 further comprising a tissue ingrowth scaffold material 210 or similar device for enabling living membrane, such as skin, at the entry site into the patient's anatomy to heal into the implantable device 200 and block the path of pathogens that would otherwise infect the patient. The modular nature of one embodiment of the present invention facilitates efficient and effective placement of the system 100, and in particular the implantable device 200 and a treatment component disposed therethrough, here depicted as a conduit system 300. Although the following detailed description references a conduit system 300 adapted for fluid flow, such as a catheter for transporting fluid to and from an external region, through the skin, and into a patient's vascular system, the conduit system 300 may be any type of elongated treatment component capable of enabling interventional therapeutic usage or diagnostic usage. Such a conduit system 300 may be for example a catheter, a fiber optic cable, an electrical power cable, or any other type of energy transmission system extending either from an external region to an internal region of a patient, or from one region of a patient's internal physiology to another internal region.

As shown in FIG. 1, an embodiment of the system 100 comprises an implantable device 200 comprising a base, or port, 205 that is adapted for placement within a patient's physiology and a tissue ingrowth scaffold material 210 disposed on one or more surfaces of the port 205. The implantable device 200 may be adapted for example for subcutaneous placement for stabilizing a treatment component such as a transcutaneous conduit system 300 for long-term use. Typically, medical ports are adapted for implantation beneath a patient's skin and connect to inner physiology via an implanted conduit of some sort. Clinicians then use a needle to intermittently access these conventional port designs through the skin. By comparison, the implantable port 205 of the present invention is capable of receiving, routing, and anchoring a medical treatment component or diagnostic component, such as for example a fluid conduit, power cable or fiber optic cable, that extends through the patient's skin, through the port 205 and into the patient's internal physiology, thereby eliminating a need for intermittent access through the skin with a needle. The port 205 of the present invention is shaped to maximize comfort and ease of installation, and thus a relatively flat and generally rectangular geometry is most suitable for a variety of applications. In embodiments, the implantable port 205 is manufactured from a biocompatible material or a combination of materials chosen from a group consisting of thermoset polymers, polyurethane, polysulfone, polycarbonate, silicone, stainless steel, and titanium. Additionally, the port 205 of the present invention is adapted to support, direct, and anchor the treatment component, such as the conduit system 300, so that no connections are required between the port 205 and the treatment component, thereby enabling fluid, light, energy or other therapeutic or diagnostic matter to flow seamlessly through the treatment component without directly contacting the port 205.

The port 205 further comprises a tissue ingrowth scaffold material 210 affixed to one or more surfaces of the port 205 for enabling tissue growth into the scaffold material 210. In one embodiment, a biocompatible adhesive secures the ingrowth scaffold material 210 to the port 205. In another embodiment, the tissue ingrowth scaffold material 210 is releasably attached, and in yet another embodiment, at least a portion of the tissue ingrowth scaffold material 210 is bioabsorbable. Preferably, at least a portion of the tissue ingrowth scaffold material 210 is bioabsorbable and secured to the port 205 by a biocompatible adhesive. The bioabsorbable portion of the tissue ingrowth scaffold material 210 may be a polymer such as but not limited to one of the following biocompatible polymers: polyglycolide, polylactide, l-lactide, poly(dl-lactide), polycolactide, poly(ε-caprolactone), polydiaxanone, polyglyconate, and poly(lactide-co-glycolide).

Figure 2A:
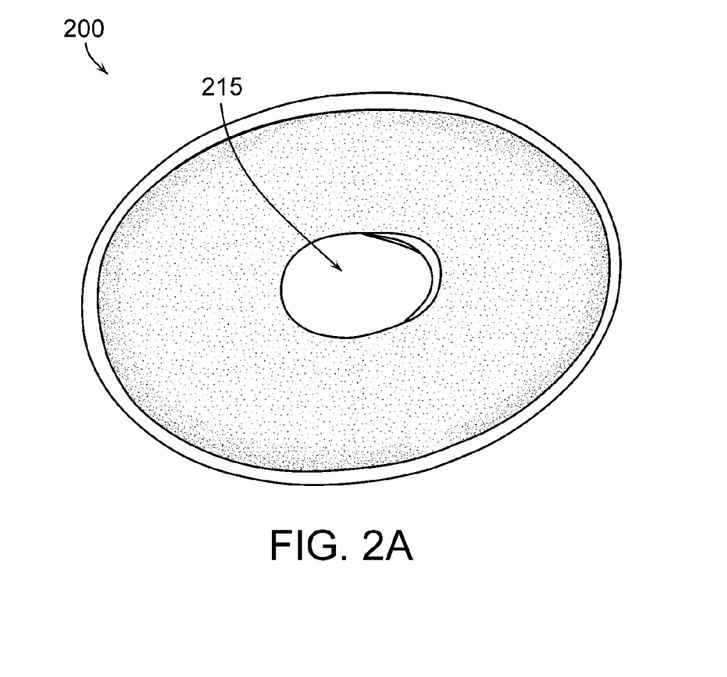
FIG. 2A depicts a top view of a unitary embodiment of the implantable port of the present invention.
Figure 2B:
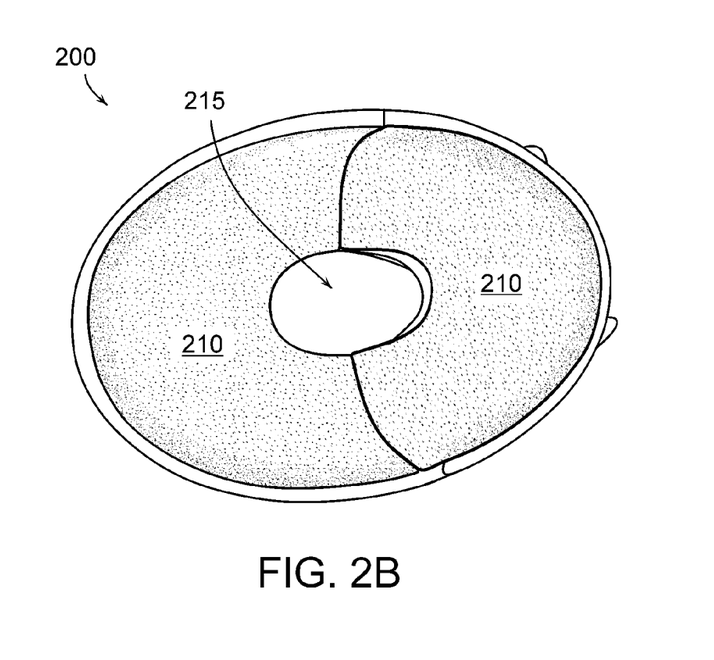
FIG. 2B depicts a top view of a modular embodiment of the implantable port of the present invention.
Figure 2C:
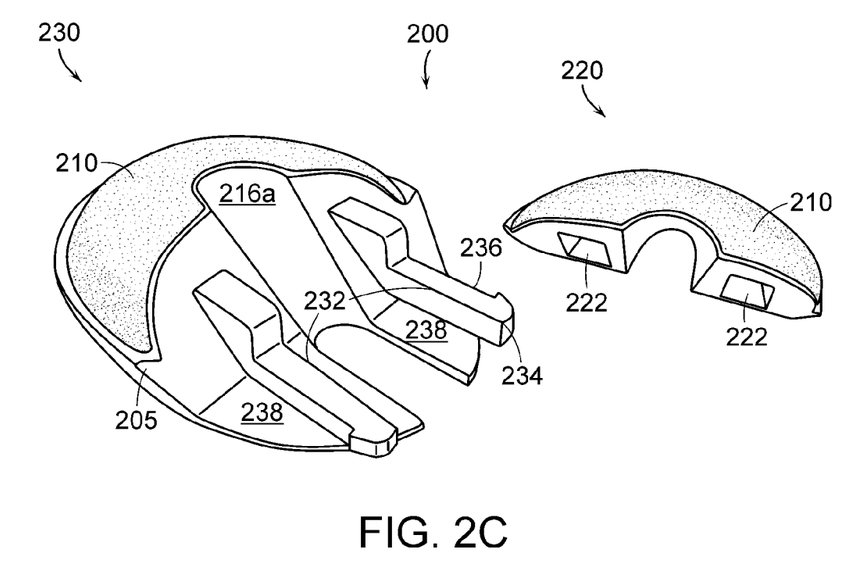
FIG. 2C depicts an exploded perspective view of a modular embodiment of the implantable port of the present invention.
Figure 2D:
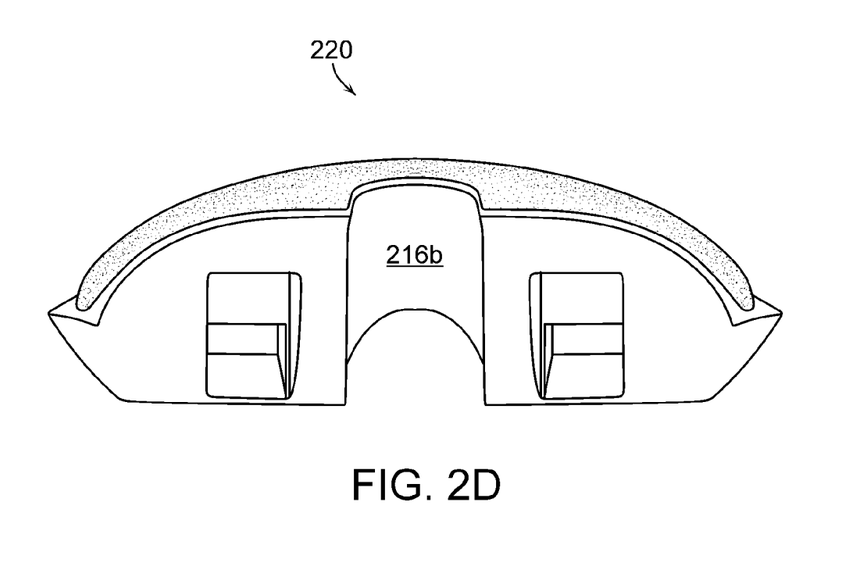
FIG. 2D depicts an end view of a modular embodiment of a portion of the implantable port of the present invention.
Figure 3A:
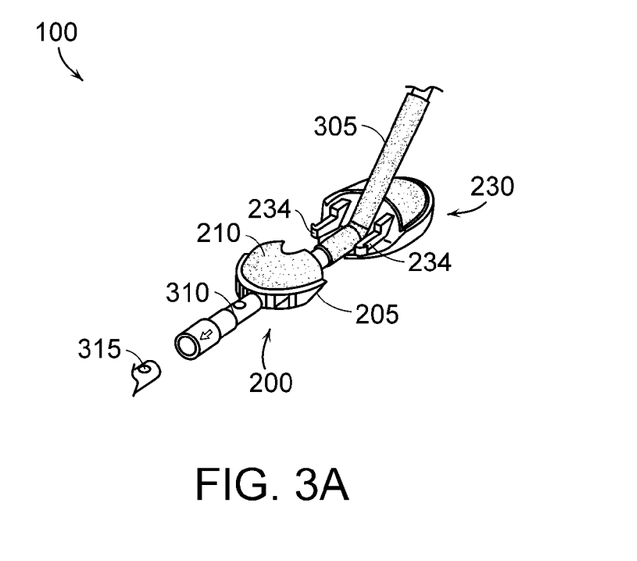
FIG. 3A depicts an exploded perspective view of an embodiment of the medical system the present invention.
Figure 3B:
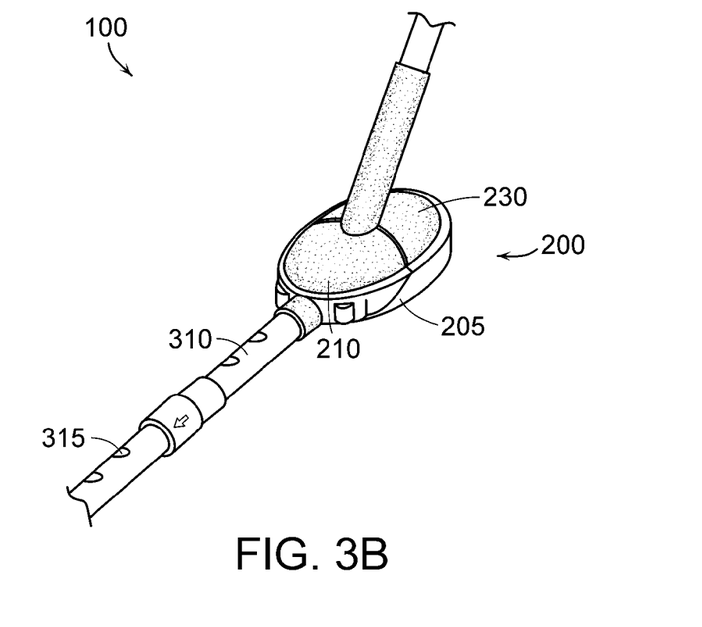
FIG. 3B depicts a perspective view of an embodiment of the medical system the present invention.

In all embodiments, unitary and modular versions of the port 205 further comprise a support passageway 215 for supporting the conduit system 300 that passes from the exterior to the interior of a patient's anatomy. For example, the unitary port 205 of FIG. 2A and the modular embodiment of the port 205 shown in FIGS. 2B through 2D depict the support passageway 215 as formed through the port 205 from one surface to another so that a continuous section of the conduit 300 may pass therethrough. In one embodiment, the support passageway 215 is angled so as to angle the trajectory of a conduit system 300 disposed therein and tunneled into the patient's inner physiology. In the present embodiment, the conduit system 300 also comprises a tissue ingrowth sleeve 305. With the conduit system 300 inserted into the support passageway 215, the tissue ingrowth sleeve 305 intersects the tissue ingrowth scaffold material 210 affixed to a surface of the port 205. As the embodiment of FIGS. 1, 3A and 3B depict in detail, the tissue ingrowth sleeve 305 is adapted for positioning within the passageway 215 so as to contact both the tissue ingrowth scaffold material 210 disposed on the upper surface of the port 205 and the living tissue around an incision site. The tissue ingrowth sleeve 305 and tissue ingrowth scaffold material 210 thereby form a continuous surface for contacting living tissue and promoting ingrowth and healing at and around the incisions into which the implantable device 200 and conduit system 300 are inserted.

In one embodiment depicted in detail in FIGS. 3A and 3B and FIGS. 6A and 6B, the conduit system 300 is modular and comprises a proximal portion 310 that passes through the port 205 and a distal portion 315 adapted for deeper insertion into a patient's anatomy. During the placement procedure, a clinician may trim the distal portion 315 to an optimal length. Once trimmed to the optimal length, the distal portion 315 connects to the proximal portion 310 for a perfectly-sized fit within the patient's physiology. In one embodiment depicted in detail in FIG. 4, the proximal portion 310 and distal potion 315 connect by means of a connector 400 that establishes a leak proof connection for uninterrupted fluid flow. This modular embodiment of the conduit system 300 is useful in cases where a distal tip 317 of the distal portion 315 has a specific design feature, such as a valve, a coating, or a particular geometrical shape requiring retention for proper use. Such a feature prevents trimming off the distal tip 317 to properly size the length of the distal portion 315. A clinician instead may trim a proximal end 319 of the distal portion 315 of the modular conduit system 300 and then connect the trimmed proximal end 319 of the distal portion 315 to the proximal portion 310.

Figure 4:
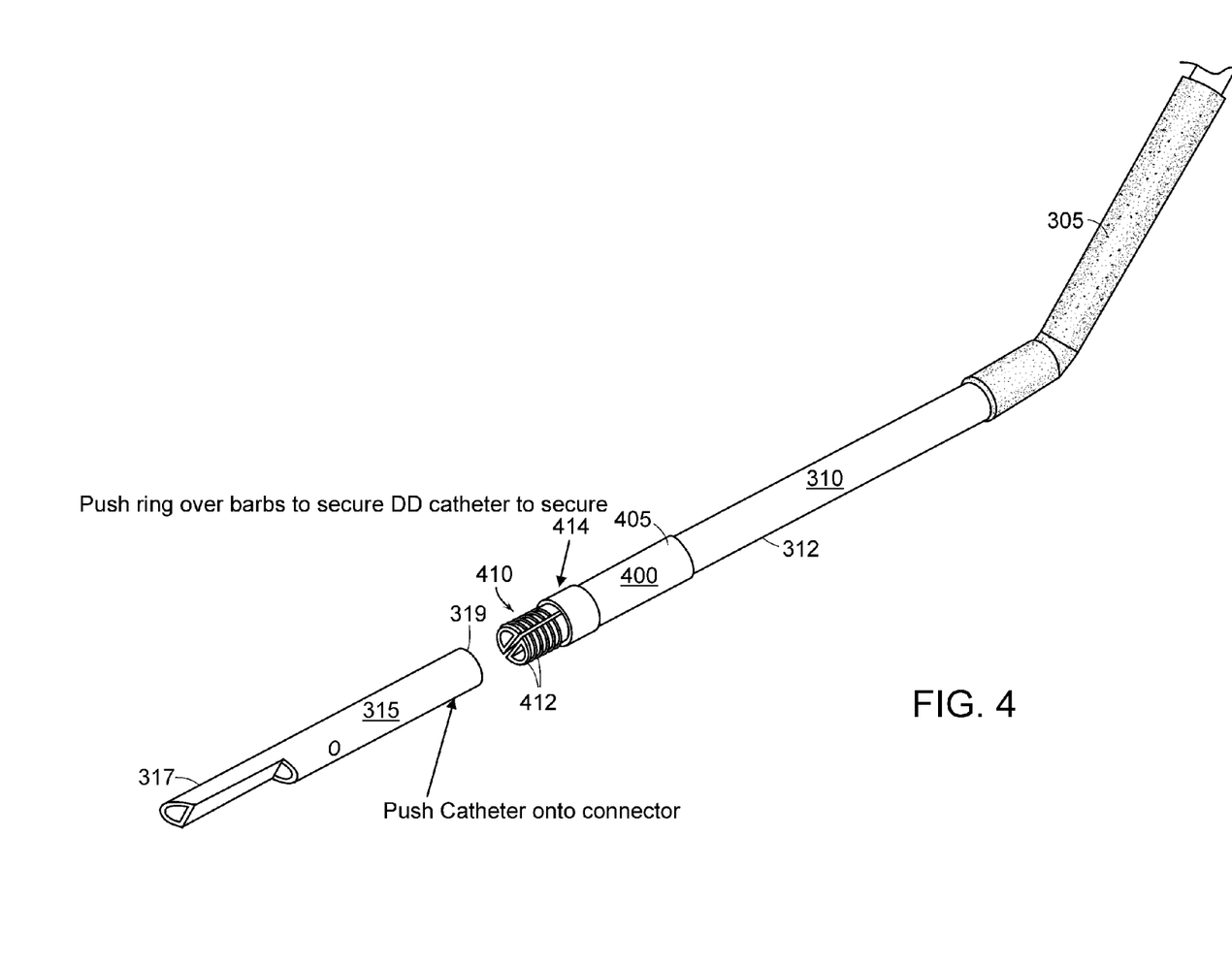
FIG. 4 depicts an embodiment of a conduit connector employed in a modular embodiment of the present invention.

FIG. 4 depicts one embodiment of a connector 400 that securely joins the trimmed distal portion 315 and the proximal portion 310 of a modular embodiment of the conduit system 300. In this embodiment, the connector 400 is sized and configured on a first end 405 for connection with the proximal portion 310 and sized and configured on a second end 410 for connection with the distal portion 315 of the modular conduit system 300. A clinician may preassemble the first end 405 with the proximal portion 310 prior to insertion into the port 205 and later assemble the second end 410 of the connector 400 with the distal portion 315 during the placement procedure. In the embodiment of FIG. 4, the second end 410 of the connector 400 is shaped for insertion into a double-D conduit configuration. In this configuration, fluid flows through the conduit system 300 within two back-to-back D-shaped inner passageways. The first end 405 of the connector 400 fits over the back-to-back D-shaped inner passageways of the distal end 312 of the proximal portion 310 and the second end 410 of the connector firmly inserts into the D-shaped inner passageways of the distal portion 315. In one embodiment, the second end 410 of the connector 400 may further comprise barbs 412 for securely grasping the inner wall of the D-shaped inner passageways of the distal portion 315. Additionally, the connector 400 may further comprise a push ring 414 that slideably engages the outer surface of the proximal end 319 of the distal portion 315 to further ensure a secure, leak proof connection between the second end 410 of the connector 400 and the distal portion 315 of the modular catheter system 300. In yet another embodiment, the connector 400 may be preassembled to the distal portion 315. Having the connector 400 preassembled to the distal portion 315 thus enables the clinician to adjust the final length of the assembled conduit system 300 by trimming the distal end 312 of the proximal portion 310, which typically has no staggered tip or other specialized geometry requiring retention. In all embodiments, the connector 400 may comprise readily identifiable features that enable a clinician to accurately locate the connector 400 following implantation under the skin. For example, the connector may comprise a textured surface that appears under ultrasonic examination. Accurate identification of the location of the connector 400 would enable a clinician to make a skin incision adjacent to the connector 400 to regain access to the connector system 300. This may be useful, for example, for the purpose of replacing the distal conduit 315 in the event of a malfunction, such as an occluded distal tip 317, without disturbing the tissue ingrowth regions of the port 205 and proximal portion 310 of the connector system 300.

Such a connector 400 enables several useful combinations of distinct design characteristics of the distal portion 315 and proximal portion 310 of the modular conduit system 300. For example, as FIG. 6B indicates, in one embodiment, the proximal portion 310 comprises a proximal cross sectional area B$\theta$ that may be larger than the distal cross sectional area A$\theta$ of the distal portion 315, and the first end 405 and second end 410 of the connector are sized accordingly to receive the proximal cross sectional area B$\theta$ and distal cross sectional area A$\theta$. This relative enlargement of the proximal portion 310 will enhance the flow rate capabilities of the assembled conduit system 300. Increasing the flow rate capability in this way enables a safe reduction in the distal cross sectional area A$\theta$ of the distal portion 315. A smaller distal portion 315 requires a less invasive insertion and smaller venotomy within the patient's physiology. Additionally, the modular embodiment of the conduit system 300 enables individual adjustment of the wall thicknesses in both the proximal portion 310 and distal portion 315. This selective optimization enables improved kink resistance of the assembled conduit system 300. Thus, the modular embodiment of the conduit system 300 enables an optimization and balance of three critical criteria: flow rate, kink resistance, and venotomy size.

Turning now to the design characteristics of the implantable device 200, in one embodiment, the implantable device 200 may be a unitary device. A clinician may implement this unitary embodiment of the implantable device 200 in cases in which the conduit system 300 comprises no connector 400 or other element sized too large for insertion through the support passageway 215 of the port 205. In one embodiment of the implantable device 200, the port 205, as depicted in FIG. 2A, is a unitary device comprising a support passageway 215 formed therethrough and extending between and through two surfaces of the port, such as an upper surface and a lower surface. The support passageway 215 formed therein is sized and shaped for receiving an elongated conduit system 300 that slideably inserts therethrough. Additionally, one embodiment of the implantable device 200 further comprises a tissue ingrowth scaffold material 210 fixedly disposed on at least a portion of the upper surface of the port 205 so that a clinician may position the tissue ingrowth scaffold material 210 against an upper inner surface of the subcutaneous pocket to promote and enable tissue ingrowth and skin healing. In other embodiments, the tissue ingrowth scaffold material 210 may be fixedly disposed on another surface of the port 205 for positioning adjacent living tissue other than dermal tissue, such as internal organ tissue, for example, to enable and promote tissue ingrowth there. In other embodiments, the tissue ingrowth scaffold material 210 may be fixedly disposed on more than one discreet surface of the port 205 for promoting more than one area of tissue ingrowth with more than one adjacent area of living tissue.

The support passageway 215 of a unitary embodiment of the implantable device 200 further comprises an inner wall 216 that is substantially continuous and firmly grips the continuous portion of the elongated conduit. In one embodiment, a clinician may apply a biocompatible adhesive to the inner wall 216 for retaining the elongated conduit system 300 therein disposed. In another embodiment, the inner wall 216 of the support passageway 215 may comprise one or more gripping elements, such as but not limited to a plurality raised bumps or a plurality of raised ridges or raised rings adapted for retaining the conduit system 300 by friction force. In such an embodiment, a clinician may adjust the conduit system 300 within the passageway 215 by applying sufficient force to overcome frictional forces that otherwise retain the conduit system 300 in a secure, immobile position during tissue ingrowth and healing.

In the embodiment of FIGS. 3A and 3B, the implantable device 200 is modular and thereby configured to accommodate a conduit system 300 having a connector 400 that is too large to fit through the support passageway 215. The modular embodiment of the implantable device 200 comprises a modular embodiment of the port 205 further comprising a distal port component 220 and a proximal port component 230 that engage to form the complete port 205. Both the distal port component 220 and proximal port component 230 have thereon biocompatible tissue ingrowth scaffold material 210. This embodiment allows a clinician to align the conduit system 300 with the proximal port component 230 such that the connector 400 is disposed beyond the port 205 following subsequent engagement of the distal port component 220 with the proximal port component 230. In one embodiment, this engagement of the proximal port component 230 and distal port component 220 of the port 205 further comprises encircling the tissue ingrowth sleeve 305 disposed on the proximal portion 310 of the conduit system 300. This further establishes a continuous surface of tissue ingrowth scaffold material 210 disposed on the distal port component 220 and the proximal port component 230 and about the proximal portion 310 of the conduit system 300. This continuous surface comprising the tissue ingrowth scaffold material 210 and the tissue ingrowth sleeve 305 provides an opportunity for living tissue adjacent to all incision sites to grow fully into the system 100 and thereby create a barrier that prevents infection.

FIGS. 2C through 3A detail one embodiment the modular implantable device 200 having a distal port component 220 and a proximal port component 230 sized and shaped for insertion into a patient's anatomy and designed for reversible engagement around a continuous portion of a conduit system 300. In one embodiment, the proximal port component 230 comprises engagement elements which cooperate with counterpart engagement elements on the distal port component 220 for aligning and securely-but-reversibly engaging the proximal port component 230 with the distal port component 220 so as to form a unified, firmly engaged, stable port 205. The engagement elements and counterpart engagement elements may comprise any number of components capable of repeated disengagement and secure repeated engagement such as but not limited to snap fit mechanisms, pressure fit elements, and hook and latch features.

Additionally, in one embodiment, the engagement elements may include features that enable a clinician to assemble the modular port 205 in stages. In such an embodiment, the clinician may align the proximal port portion 230 and the distal port portion 220 in a semi-connected position such that the support passageway 215 is loosely formed around the conduit system 300, and the conduit system 300 may move freely in the support passageway 215. Once the clinician optimizes the position of the conduit system 300 and, in certain embodiments, the ingrowth sleeve 305 thereon relative to the support passageway 215 of the base 205, the clinician may fully engage the loosely connected proximal port portion 230 and the distal port portion 220 to securely support the conduit system 300 therein positioned. In its fully assembled state, one embodiment of the modular embodiment port 205 exerts a compressive force onto the conduit system 300 to prevent movement and anchor the conduit system 300 while still enabling uninterrupted fluid flow through the conduit system 300. Additionally, in another embodiment, the modular port 205 may be supplied to a clinician initially in a semi-connected position such that the clinician may not disassemble the port 205 and so that perfect alignment of the engagement elements and counterpart engagement elements on the distal port component 220 and proximal port component 230 already exists prior to insertion into a patient's physiology. This pre-aligned modular port 205 embodiment further aids a clinician in easily and accurately installing the port 205 and conduit system 300.

In the embodiment of FIGS. 2C through 3A, the engagement elements comprise interlocking elements and the counterpart engagement elements comprise receiving portions that are aligned to receive the interlocking elements. Specifically, the engagement elements comprise a plurality of tines 232 and the counterpart engagement elements comprise a plurality of slots 222 sized for securely receiving the plurality of tines 232. The plurality of tines 232 are offset slightly from the plurality of slots and once engaged with the plurality of slots 222, the plurality of tines 232 apply an outward force against an inner wall of the corresponding plurality of slots 222. The plurality of tines 232 therefore remain securely positioned within the plurality of slots 222 as depicted in FIGS. 1, 2B and 3B. In one embodiment, each of the plurality of tines 232 further comprises a bulbous, or barbed, end 234 having at least one angled or curved sidewall for guiding each of the plurality of tines 232 into a corresponding slot 222. Each bulbous end 234 further may comprise an undercut portion 236 such that following engagement of the plurality of tines 232 within the plurality of slots 222, each bulbous end 234 extends beyond the periphery of each corresponding one of the plurality of slots 222 and each corresponding undercut portion 236 presses against an outside wall of each of the plurality of slots 222. The undercut portion 236 thereby prevents the corresponding tine 232 from retracting from a slot 222 without an application of inward force that counteracts the outward force emanating from the offset plurality of tines 232 and that pushes the undercut portion 236 of the barbed end 234 inside the slot 222.

A clinician thus may selectively disassemble the modular embodiment of the port 205 by squeezing the bulbous ends 234 of the plurality of tines 232 toward one another to counteract the outward force imparted by the plurality of tines 232. Applying such force to the bulbous ends 234 thus allows the plurality of tines 232 to realign with the plurality of slots 222 so that the distal port component 220, which is no longer retained by the bulbous ends 234 and outward forces of the plurality of tines 232 disposed within the plurality of slots 222, freely disengages from the proximal port component 230. As FIGS. 1, 2B and 3B depict, the bulbous ends 234 are readily accessible to a clinician when the modular port 205 is assembled, and the clinician may access the bulbous ends 234 easily, readily imparting an inward force using fingertips or a surgical forceps, for example.

In addition to comprising engagement elements that produce a secure and reversible engagement between the proximal port component 230 and distal port component 220, one embodiment of the port 205 further provides a shelf portion 238 above which the plurality of tines 232 extend. The shelf portion 238 receives the distal port component 220 thereon during engagement of the distal port component 220 and the proximal port component 230. FIG. 2C depicts the shelf portion 238 which helps align and stabilize the two base (port) components during and after assembly. Additionally, in one embodiment, the port 205 is shaped for comfortable use, and the distal port component 220 and the proximal port component 230 each have a contoured upper surface to facilitate insertion into and removal from a patient's physiology. In one embodiment, the port 205 is substantially oval shaped and disk shaped such that its length is greater than its thickness, thereby providing a sturdy base for securing the conduit system 300 while imparting minimal trauma upon the patient. Additionally, the port 205 is preferably manufactured from a biocompatible material such as but not limited to thermoset polymers, polyurethane, polysulfone, polycarbonate, silicone, stainless steel, and titanium. The port 205 and any modular components thereof may be machined, extruded, injection molded or produced by any process, or combination of processes, enabling the formation of the critical elements and features herein described.

The distal port component 220 and the proximal port component 230 are thus designed for reversible but secure engagement, and the port 205 is designed for comfort during use. The support passageway 215 of the port 205 further enhances comfort and support. In modular embodiments, the distal port component 220 and the proximal port component 230 each further comprise a portion of a wall 216 defining the support passageway 215. The proximal portion wall 216a and the distal portion wall 216b cooperate to define the support passageway 215 when the proximal port component 230 and distal port component 220 are assembled in an engaged state. The support passageway 215 thus is formed by assembling the distal port component 220 and the proximal port component 230 and is sized to accommodate a continuous portion of the conduit system 300 that passes through the port 205 from one surface to another. In all embodiments, the wall 216 of the support passageway 215 is substantially continuous and firmly grips the continuous portion of the catheter system 300 to secure that treatment component in place. The modular embodiment of the port 205 thus enables a clinician to disassemble the port 205 and further adjust the proximal portion 310 of the conduit system 300 by sliding the proximal portion 310 forward or backward as needed and then reassembling the distal port component 220 and the proximal port component 230 about the proximal portion 310

In addition to enabling adjustment of the conduit system 300, the port 205 of the present invention provides a support passageway 215 that is sized to enable uninterrupted fluid flow through the conduit system 300 when the conduit system 300 is designed for such fluid flow, for example in cases in which the conduit system 300 comprises a catheter. Furthermore, in one embodiment, the longitudinal access of the support passageway 215 is angled between 0 and 90 degrees relative to upper surface of the port 205. In preferred embodiments, the longitudinal axis of the support passageway 215 is angled between 35 and 55 degrees from the upper surface of the port 205. FIGS. 2B through 2D depict the proximal portion wall 116a and the distal wall portion 116b which combine to form the angled support passageway 215. The embodiment of the present invention having an angled support passageway 215 enables a more ergonomic use of the system 100 when implanted within a patient. Because the support passageway 215 is angled, the conduit system 300 exits the port 205 and the patient's physiology at an angle that enables comfortable positioning of the proximal portion 310 against the patient's body. This positioning prevents any application of uncomfortable torque on the conduit system 300 when implanted within the patient and maintains proper alignment of the conduit system without imparting any disruptive bends or kinks that might otherwise disrupt a smooth fluid flow through the conduit system 300.

Turning now to a method of implanting and deploying the system 100, the present invention is adapted for use across all patient sizes. Many non modular conduit designs, such as standard Hemodialysis catheters, cannot be trimmed because their distal ends have special tip geometries, and clinicians, therefore, must stock various preset lengths of conduit. Generally, proximal ends of conduits also cannot be trimmed because of assembly fittings that enable connections to dialysis machines. Manufacturers thus produce such catheters in a range of pre-determined, pre-cut lengths which may or may not fit perfectly within a particular patient's physiology. A clinician then must choose the length that most closely suits a patient's physiology. The need to stock multiple lengths of the same product is a disadvantage that is overcome by the modular approach of one embodiment of the system 100 of the present invention.

Figure 5A:
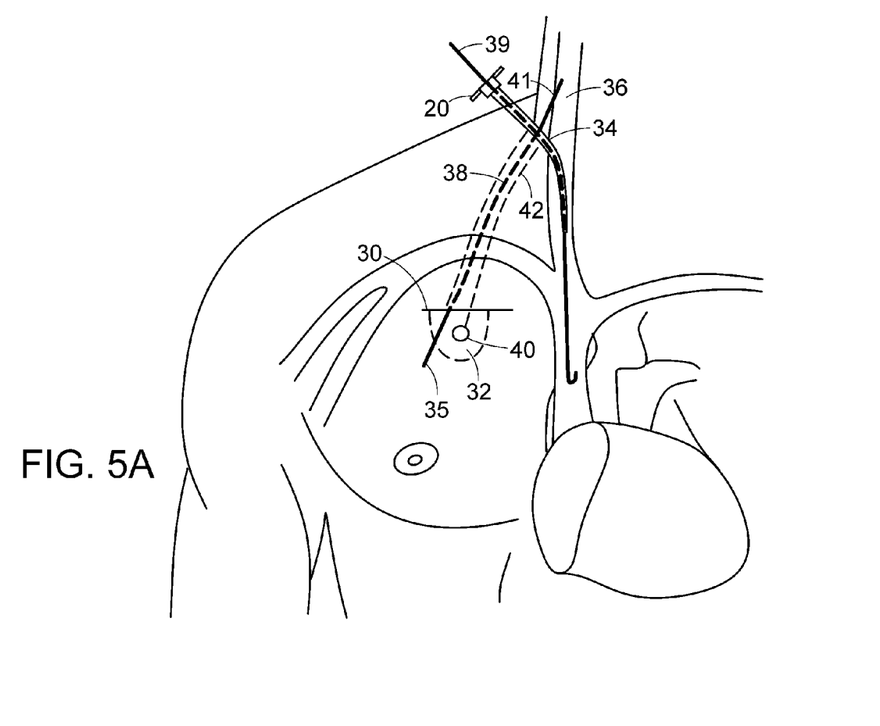
FIG. 5A depicts a front view of the preparations made to a patient prior to implantation of an embodiment of the medical system of the present invention.

Interventional Radiologists, Vascular Surgeons, or Interventional Nephrologists are the types of clinicians who would place the system 100 of the present invention within a patient's physiology. Typically, a clinician prepares a patient for the procedure by thoroughly disinfecting the skin site and applying local anesthesia. As shown in FIGS. 5A, in one embodiment of the method of implanting the system 100, the clinician prepares a patient for implantation of the system 100 by creating a skin incision 30 and forming a subcutaneous pocket 32 by blunt dissection. The subcutaneous pocket 32 is created to receive the port 205. Using ultrasound guidance, the clinician then forms a venotomy 34 in the patient's internal jugular vein 36 using a micropuncture set (not shown) and Seldinger technique. The clinician then enlarges the venotomy 34 by switching out the micropuncture set for a guidewire 39 and peelable introducer sheath/dilator set 20 of sufficient size to accommodate the conduit system 300. The clinician introduces a sharp tunneler tip 41 of the tunneling device 38 into the subcutaneous pocket 32 below the incision 30 and forcefully pushes the tunneler tip 41 under the skin towards the venotomy 34, thereby creating a subcutaneous tunnel 42. (The conduit system 300 eventually will travel through the subcutaneous tunnel 42 between the venotomy 34 and the pocket 32.) The clinician then makes a small incision above the venotomy 34 to allow the tunneler tip 41 to protrude through the skin for eventual removal from the subcutaneous tunnel 42 at the venotomy 34 site. The clinician will leave the tunneling device 38 temporarily in place within and across the subcutaneous tunnel 42 while preparing the conduit system 300 for positioning.

Figure 5B:
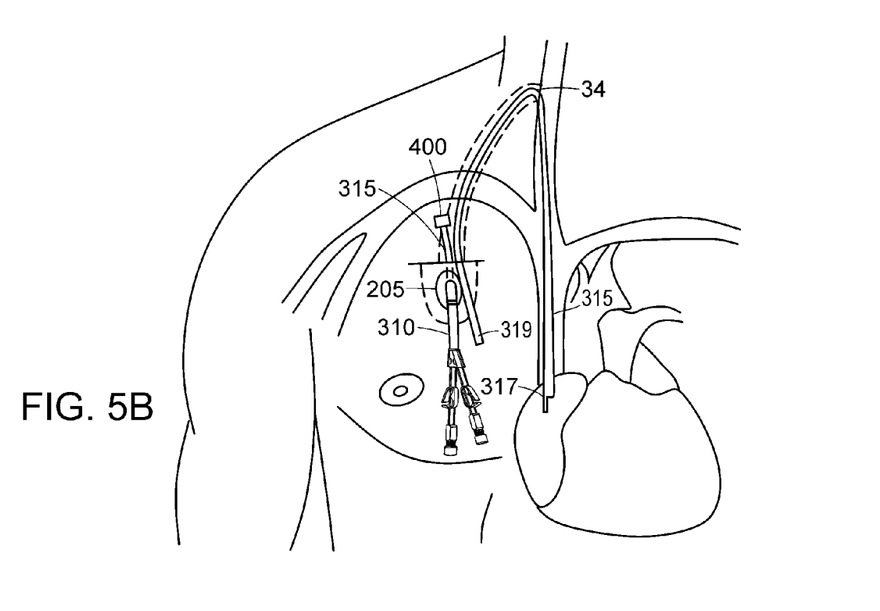
FIG. 5B depicts a front view of a patient during the process of implanting an embodiment of the medical system of the present invention.

If the distal tip 317 of the distal portion 315 of the conduit system 300 lacks a specialized tip feature, the clinician simply may trim the distal tip 317 to the required length for proper fit within the patient. In this instance, the conduit system 300 need not be modular and may be unitary. First, as FIG. 5B depicts, the clinician will insert the port 205 into the subcutaneous pocket 32 and form a skin opening 40 in the dermis above the subcutaneous pocket 32 through which the proximal portion 310 of the conduit system 300 will pass. The clinician then will insert the conduit system 300 through the skin opening 40, through the support passageway 215 and out through the skin incision 30 that defines one edge of the subcutaneous pocket 32. The clinician then will attach the distal tip 317 of the distal portion 315 of the conduit system 300 to a barbed end 35 of the tunneling device 38, and pull the tunneling device 38 out of the subcutaneous tunnel 42 by the sharp tunneler tip 41 at skin puncture site for the venotomy 34. Pulling the tunneling device 38 out of the subcutaneous tunnel 42 also pulls the attached distal portion 315 into and through the subcutaneous tunnel 42. Once the distal tip 317 travels completely through the subcutaneous tunnel 42, the clinician will disconnect the distal portion 315 from the tunneler tip 41 and discard the tunneling device 38.

Once the conduit system 300 is initially positioned within the tunnel 42, the clinician then may adjust the tissue ingrowth sleeve 305 to an optimal location relative to the port 205 and the skin opening 40. The clinician thus ensures that the tissue ingrowth scaffold material 210 and the tissue ingrowth sleeve 305 form a continuous tissue ingrowth surface that directly contacts the upper inside surface of the subcutaneous pocket 32 surrounding the skin opening 40 and also directly contacts the surfaces of the skin opening 40 to promote and enable tissue ingrowth and skin healing that prevents infection at all incision sites.

With the proximal portion 310 properly adjusted, the clinician will then trim the distal tip 317 of the distal portion 315 so that the distal portion 315 will resides in a desired location within the patient once the clinician completes insertion of the distal portion 315 into the venotomy 34. Next, the clinician will remove the guidewire 39 and dilator from the peelable introducer sheath 20 and immediately insert the trimmed distal portion 315 of the conduit system 300 through the peelable introducer sheath 20. The clinician then will advance the distal portion 315 into the internal jugular vein 36 and deeper into the vascular system to the desired location. Once the distal tip 317 reaches its proper position, the clinician will make any needed adjustments to the conduit position and test the device for proper function. The clinician then will remove the peelable introducer sheath 20 by peeling it away from the distal portion 315 and out of the venotomy 34. The clinician will suture the skin incision 30 to close the subcutaneous pocket 32. The clinician also will suture the smaller incision at the venotomy 34 site to complete the placement procedure of the system 100 within a patient's physiology.

By comparison, if the conduit system 300 has a specialized feature on the distal tip 317 that precludes trimming that end of the distal portion 315, a modular conduit system 300 comprising special trimming guides is preferred so that a clinician may adjust the length of the conduit system 300 by trimming the a proximal end 319 of the distal portion 315 without impacting the distal tip 317, already positioned within the patient's physiology. Additionally, if the connector 400 is larger than the support passageway 215, then a clinician may use the modular embodiment of the port 205 which has a proximal port portion 230 and a distal port portion 220 designed for reversible engagement. In one embodiment, a method of using the modular embodiment of the port 205 and modular conduit system 300 comprises first inserting the proximal port component 230 into the subcutaneous pocket 32 so that the tissue ingrowth scaffold material 210 is positioned against an inner tissue surface of the upper, outer flap of the subcutaneous pocket 32. Next, the method comprises forming a skin opening 40 in the dermis above the subcutaneous pocket 32 through which the conduit system 300 will pass. A clinician then inserts the proximal portion 310 and connector 400 through the skin opening 40, into the subcutaneous pocket 32, past the proximal port component 230, and out though the skin incision 30 that defines one edge of the subcutaneous pocket 32.

Just as described above, the method then comprises attaching the distal tip 317 of the distal portion 315 of the conduit system 300 to a barbed end 35 of a tunneling device 38. The clinician will advance the sharp tunneler tip 41 of the tunneling device 38 from the skin incision 30 towards the venotomy 34, thereby pulling the distal portion 315 into and through a subcutaneous tunnel 42. Once the distal portion 315 is positioned within the subcutaneous tunnel 42, a clinician will disconnect and discard the tunneling device 38. The clinician will adjust the position of the tissue ingrowth sleeve 305 to an optimal location relative to the proximal port component 230 and the skin opening 40. Next, the method comprises inserting the distal port component 220 into the subcutaneous pocket 32 and connecting that distal port component 220 to the proximal port component 230 by sliding the plurality of slots 222 over the plurality of tines 232 until the plurality of barbs 234 snap into place. The clinician may press the distal wall portion 216b of the support passageway 215 over the distal portion 315 of the conduit system 300 and slide the distal port component 220 along the distal portion 315 until the distal port component 220 aligns with and fully engages the proximal port component 230. Alternatively, in some embodiments, the clinician may opt to assemble the modular port 205 into an intermediate closure position which allows the clinician to further adjust the proximal portion 310 if needed while completing the placement procedure and before fully engaging the components of the modular port 205.

Once the distal port component 220 fully engages with the proximal port component 230, the unified port 205 comprises a continuous surface comprising the tissue ingrowth scaffold material 210 disposed on the port components 220, 230, and the tissue ingrowth sleeve 305 affixed to the proximal portion 310 of the conduit system 300. In one embodiment, at least a section of the tissue ingrowth sleeve 305 of the proximal portion 310 of the conduit system 300 is positioned between the distal port component 220 engaged with the proximal port component 230 and another section is positioned through the skin opening 40. A continuous surface of tissue ingrowth scaffold material 210 therefore directly contacts an upper, inner surface of the subcutaneous pocket 32 surrounding the skin opening 40. Additionally, the tissue ingrowth sleeve 305 directly contacts the surfaces of the skin opening 40. This continuous contact between tissue ingrowth scaffold material 210 and the tissue ingrowth sleeve 305 with living tissue at and around the incision sites promotes and enables tissue ingrowth and healing that prevents infection at all incision sites. Lastly, the clinician will bring the distal end 312 of the proximal portion 310 outside of the patient via the skin incision 30 so that the connector 400 is easily reachable during assembly of the modular conduit system 300.

Figure 6A:
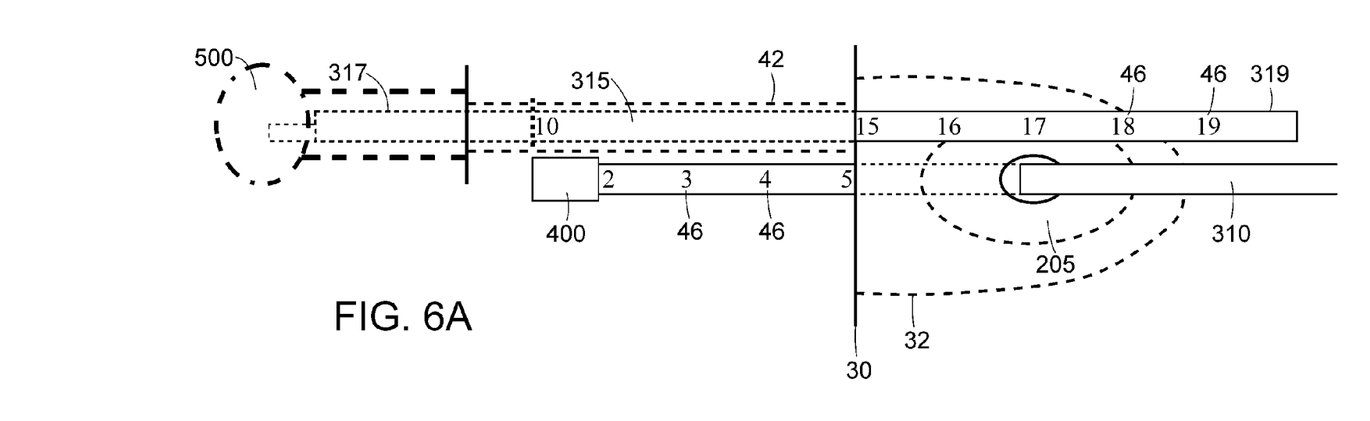
FIG. 6A depicts a schematic plan view of a modular embodiment of the medical system of the present invention after implantation and during measurement of the modular conduit prior to trimming.
Figure 6B:
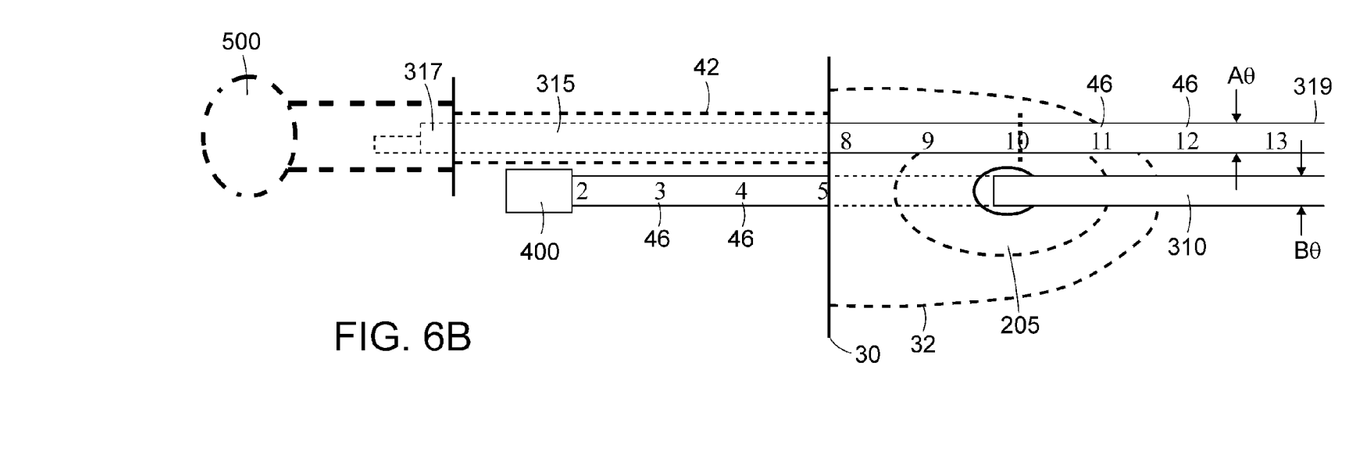
FIG. 6B depicts a schematic plan view of a modular embodiment the medical system of the present invention following measuring and retracting a portion of modular conduit in preparation for trimming.

Once the proximal portion 310 is positioned within the proximal port component 230 and once the proximal port component 230 and distal port component 220 are engaged, the clinician will advance the distal tip 317 of the distal portion 315 of the conduit system 300 deep into the patient's vascular system through the peelable introducer sheath 20, until the distal tip 317 reaches a desired location 500 within the patient's vascular system, and the sheath can be removed. The excess length of the fully inserted distal conduit 315 extends outside of the patient at the pocket incision and aligns with the distal end 312 of the proximal portion 310 as shown in FIGS. 5B, 6A, and 6B. Because the conduit system 300 is modular and marked for trimming, a clinician may easily and accurately size and position the distal portion 315 of this embodiment of the catheter system 300 within a patient's physiology while preserving a specialized feature of the distal tip 317. FIGS. 6A and 6B depict one embodiment of the method of sizing and placing the distal portion 315 prior to connecting the distal portion 315 and proximal portion 310 via the connector 400 or some other connection means.

FIG. 6A depicts the inserted distal portion 315 and proximal portion 310 of a modular embodiment of the conduit system 300 in relation to the subcutaneous pocket 32 and skin incision 30. In one embodiment, both the distal portion 315 and proximal portion 310 comprise graduated markings 46 that enable a clinician to determine where to trim the proximal end 319 of the distal portion 310. With the distal tip 317 disposed in a desired location 500 and with the connector 400 aligned adjacent to and/or resting directly over the subcutaneous tunnel 42 and outside a patient's body, a clinician may determine a point at which to trim the distal portion 315 so that the distal portion 315 and proximal portion 310 engage to form a continuous length that fits perfectly inside the tunnel 42 so that the distal tip 317 ultimately remains correctly positioned at the desired location 500. A clinician may note the graduated marking 46 on the proximal portion 310 that most closely aligns with the skin incision 30 at the entrance to the subcutaneous pocket 32. The clinician then may note the visible graduated marking 46 on the distal portion 315 that aligns most closely to the skin incision 30. In one embodiment, the graduated markings 46 that comprise this novel measurement system are arranged such that subtracting the graduated marking 46 noted on the proximal portion 310 from the graduated marking 46 noted on the distal portion 315 provides guidance on where to trim the proximal end 319 of the distal portion 315 so that the distal portion 315 and proximal portion 310 engage to form an exact length needed to ensure proper placement of the distal tip 317 in the desired location 500. As the example in FIG. 6A depicts, the distal portion 315 exhibits a graduated marking 46 reading "15" at the incision 30, and the proximal portion 310 exhibits a graduated marking 46 reading "5" at the incision 30. Subtracting "5" from "15" guides the clinician to trim the proximal end 319 of the distal portion 315 at the graduated marking 46 reading "10" to ensure proper placement of the distal tip 317 once the distal portion 315 connects to the proximal portion 310.

As FIG. 6B depicts, the clinician may then partially retract the distal portion 315 of the conduit system 300 from the subcutaneous tunnel 42 to expose the calculated graduated marking 46 at which the clinician will trim the distal portion. Once the clinician trims the proximal end 319 of the distal portion 310, the clinician may connect the distal portion 315 to the proximal portion 310 via the connector 400 and visually inspect and test the connector 400 to ensure proper alignment of the distal portion 315 and proximal portion 310 and to ensure a fluid tight connection. If necessary, the clinician can detach the distal port component 220 from the proximal port component 230 either fully or partially while retracting or advancing the proximal portion 310 as needed to facilitate the connection with the distal portion 315 of the conduit system 300. The clinician then may advance the connector 400 into the subcutaneous tunnel 42 until the conduit system 300 is straight and the distal tip 317 returns to the desired location 500 as confirmed by the proper graduated markings 46 aligning once again with the skin incision 30. If the clinician had disassembled the modular port 205 to facilitate connecting the distal portion 315 and proximal portion 320 of the conduit system 300, the clinician then would reassemble the modular port 205 around the assembled, properly re-positioned modular conduit system 300.

The modular embodiment of the conduit system 300 of the present invention thus provides a means for easily and precisely determining where to trim the distal portion 310 of the conduit system 300 to ensure proper placement of the distal tip 317. Also, this modular conduit system 300, in combination with the modular embodiment of the port 205, enables a clinician to make adjustments to the position of the proximal portion 310 and connect the distal portion 315 and the proximal portion 310 outside of the patient's body and in plain sight. This solves problems associated with devices requiring a clinician to make unseen conduit connections to a port disposed within a subcutaneous pocket positioned beneath the skin. Those devices prevent the clinician from seeing the connection components while actuating and testing them, which could lead to improper or incomplete and unreliable connections that lead to device failure. In contrast, the present invention enables a clinician to easily place a conduit system 300 in a port 205 without requiring the clinician to blindly engage conduit connections to the port 205, and this invention also provides means for easily and accurately determining where to trim the conduit for maximum safety, efficacy, and comfort to the patient. Additionally, the present invention enables the clinician to actuate and test a connection of a modular conduit system 300 in plain sight, outside of the subcutaneous pocket 32 and above the skin prior to final insertion of the conduit system 300 within the subcutaneous tunnel 42.

While the present invention has been described above with reference to its preferred embodiments, it should be understood that various permutations of these embodiments can be readily devised by those skilled in the art without departing from the scope of the present invention. For instance, embodiments with multiple conduits could be employed, or conduits with multiple channels within them, without departing from the scope of this invention. One and two section conduit designs are presented as preferred embodiments, but some embodiments may require more than two conduit components without departing from the scope of this invention. The preferred embodiment of the two component conduit marking system also could be adapted to enable clinicians to trim multiple conduit components prior to assembly without departing from the spirit of this invention.

The sequence of steps for the placement procedure described above is generally suitable for placing different embodiments of this invention within a patient's vascular system. This invention clearly is suitable for use in other types of medical procedures that do not involve the vascular system and/or the skin that would require the clinician to employ other placement techniques and other, non-fluid carrying conduit, such as fiber optic cables, without departing from the spirit or scope of this invention. Also, the sequence of steps can be modified by those skilled in the art to still achieve the same final placement. Numerous adaptations to the preceding description can be readily devised by those skilled in the art without departing from the spirit and scope of the present invention as defined in the following claims.

I claim:

1. A modular subcutaneous assembly for stabilizing a transcutaneous catheter for long-term use, the modular subcutaneous assembly comprising:
   a) a first and second subcutaneous element sized and shaped for subdermal insertion and designed for reversible engagement around a continuous portion of a transcutaneous catheter, the first subcutaneous element comprising engagement elements which cooperate with counterpart engagement elements on the second subcutaneous element for aligning and firmly but reversibly engaging the second subcutaneous element with the first subcutaneous element, the first and second subcutaneous elements each further comprising semi-circular wall portions of a tubular support passageway divided lengthwise along the longitudinal axis which semi-circular wall portions cooperate to define a tubular support passageway when the first and second subcutaneous elements are assembled in an engaged state, the tubular support passageway formed by assembly of the first and second subcutaneous elements and being sized to accommodate a continuous portion of a transcutaneous catheter wherein the wall of the tubular support passageway is substantially continuous and grips the continuous portion of the catheter thereby stabilizing the catheter position; and b) a tissue ingrowth cuff material fixedly disposed on at least one surface of both of the first and second subcutaneous elements for securing the modular subcutaneous assembly to adjacent tissue such that the tissue ingrowth cuff material fixedly disposed on the first subcutaneous elements and the tissue ingrowth cuff material fixedly disposed on the second subcutaneous elements join to form a continuous surface when the first and second subcutaneous elements are assembled in an engaged state.

2. The modular subcutaneous assembly of claim 1 wherein the at least one surface is an upper surface and/or lower surface and the adjacent tissue is dermal tissue and/or organ tissue.

3. The modular subcutaneous assembly of claim 1 wherein at least a portion of the tissue ingrowth cuff material is releasably attached.

4. The modular subcutaneous assembly of claim 1 wherein at least a portion of the tissue ingrowth cuff material is bioabsorbable.

5. The modular subcutaneous assembly of claim 4 wherein the bioabsorbable cuff material is a polymer selected from a group consisting of polyglycolide, polylactide, I-lactide, poly (dl-lactide), polycolactide, poly(ε-caprolactone), polydiaxanone, polyglyconate, and poly(lactide-co-glycolide).

6. The modular subcutaneous assembly of claim 1 wherein the engagement elements and counterpart engagement elements are capable of repeated disengagement and secure repeated engagement.

7. The modular subcutaneous assembly of claim 1 wherein the engagement elements and counterpart engagement elements comprise a snap fit configuration.

8. The modular subcutaneous assembly of claim 1 wherein the engagement elements and counterpart engagement elements comprise a pressure fit configuration.

9. The modular subcutaneous assembly of claim 1 wherein the engagement elements and counterpart engagement elements comprise a hook and latch configuration.

10. The modular subcutaneous assembly of claim 1 wherein the engagement elements comprise interlocking elements and the counterpart engagement elements comprise receiving portions being aligned to receive the interlocking elements.

11. The modular subcutaneous assembly of claim 10 wherein the interlocking elements comprise a plurality of tines and the receiving portion comprises a plurality of slots sized for securely receiving the plurality of tines.

12. The modular subcutaneous assembly of claim 11 wherein the plurality of tines are offset from the plurality of slots and once engaged, the tines apply an outward force against an inner wall of the corresponding plurality of slots such that the plurality of tines remain securely positioned within the slots.

13. The modular subcutaneous assembly of claim 12 wherein each of the plurality of tines terminates in a bulbous end having at least one angled sidewall for guiding the tine into a corresponding slot and having an undercut portion such that following engagement of the plurality of tines within the plurality of slots, each bulbous end extends beyond the periphery of each corresponding slot and the corresponding tine cannot retract from the slot without an application of inward force that counteracts the outward force.

14. The modular subcutaneous assembly of claim 11 wherein the first subcutaneous element further comprises a shelf portion above which the plurality of tines extend such that the shelf portion receives the second subcutaneous element thereon during engagement.

15. The modular subcutaneous assembly of claim 14 wherein the bottom shelf and the second subcutaneous element engage in a mating fit.

16. The modular subcutaneous assembly of claim 1 wherein the first and second subcutaneous elements have contoured upper surfaces to facilitate insertion and removal.

17. The modular subcutaneous assembly of claim 1 wherein the cuff assembly is substantially oval shaped and disk shaped such that its length is greater than its thickness.

18. The modular subcutaneous assembly of claim 1, wherein the first and second subcutaneous elements are manufactured from a material or a combination of materials chosen from a group consisting of thermoset polymers, polyurethane, polysulfone, polycarbonate, silicone, stainless steel, and titanium.

19. The modular subcutaneous assembly of claim 1 wherein a longitudinal axis of the tubular support passageway is angled relative to upper surfaces of the first and second subcutaneous elements.

20. The modular subcutaneous assembly of claim 19 wherein the longitudinal axis of the tubular support passageway is angled preferably between 0 and 90 degrees and more preferably between 35 and 55 degrees from the upper surfaces of engaged first and second subcutaneous elements.

21. The modular subcutaneous assembly of claim 1 wherein the tubular support passageway is sized to enable uninterrupted fluid flow through the catheter.

22. The modular subcutaneous assembly of claim 1 further comprising a distal catheter portion and a proximal catheter portion adapted for modular assembly, wherein the proximal catheter portion is adapted for insertion through the tubular support passageway and the distal catheter portion is adapted for insertion into internal physiology prior to connecting the proximal catheter portion to the distal catheter portion.

23. The modular subcutaneous assembly of claim 22 further comprising a measurement marking system integrated into the distal catheter portion and proximal catheter portion so as to enable precise measuring and trimming of the distal and/or proximal portion.

24. The implantable medical device of claim 22 further comprising a connector for firmly affixing the distal catheter portion to the proximal catheter portion.

25. The implantable medical device of claim 24 wherein the distal catheter portion and the proximal catheter portion comprise different cross sectional geometries and the connector is sized to accommodate both geometries and enable uninterrupted fluid flow.

* * * * *